US00PP24737P3

(12) United States Plant Patent
Dibley

(10) Patent No.: US PP24,737 P3
(45) Date of Patent: Aug. 5, 2014

(54) ***STREPTOCARPUS* PLANT NAMED 'SLSBW10-0'**

(50) Latin Name: ***Streptocarpus* hybrid**
Varietal Denomination: SLSBW10-0

(71) Applicant: Lynne Dibley, Ruthin (GB)

(72) Inventor: Lynne Dibley, Ruthin (GB)

(73) Assignee: Dibley's Nurseries (GB)

( * ) Notice: Subject to any disclaimer, the term of this patent is extended or adjusted under 35 U.S.C. 154(b) by 11 days.

(21) Appl. No.: 13/694,734

(22) Filed: Dec. 27, 2012

(65) Prior Publication Data

US 2014/0189916 P1 Jul. 3, 2014

(51) Int. Cl.
*A01H 5/00* (2006.01)

(52) U.S. Cl.
USPC ..... Plt./333

(58) Field of Classification Search
USPC ..... Plt./333
See application file for complete search history.

*Primary Examiner* — Anne Grunberg
(74) *Attorney, Agent, or Firm* — Cassandra Bright

(57) ABSTRACT

A new and distinct *Streptocarpus* cultivar named 'SLSBW10-0' is disclosed, characterized by small, pale violet-purple colored flowers and multi-flowering, 6-8 per inflorescence. The new variety is a Streptocarpus, suitable as an outdoor garden or container plant.

2 Drawing Sheets

Figure 1:
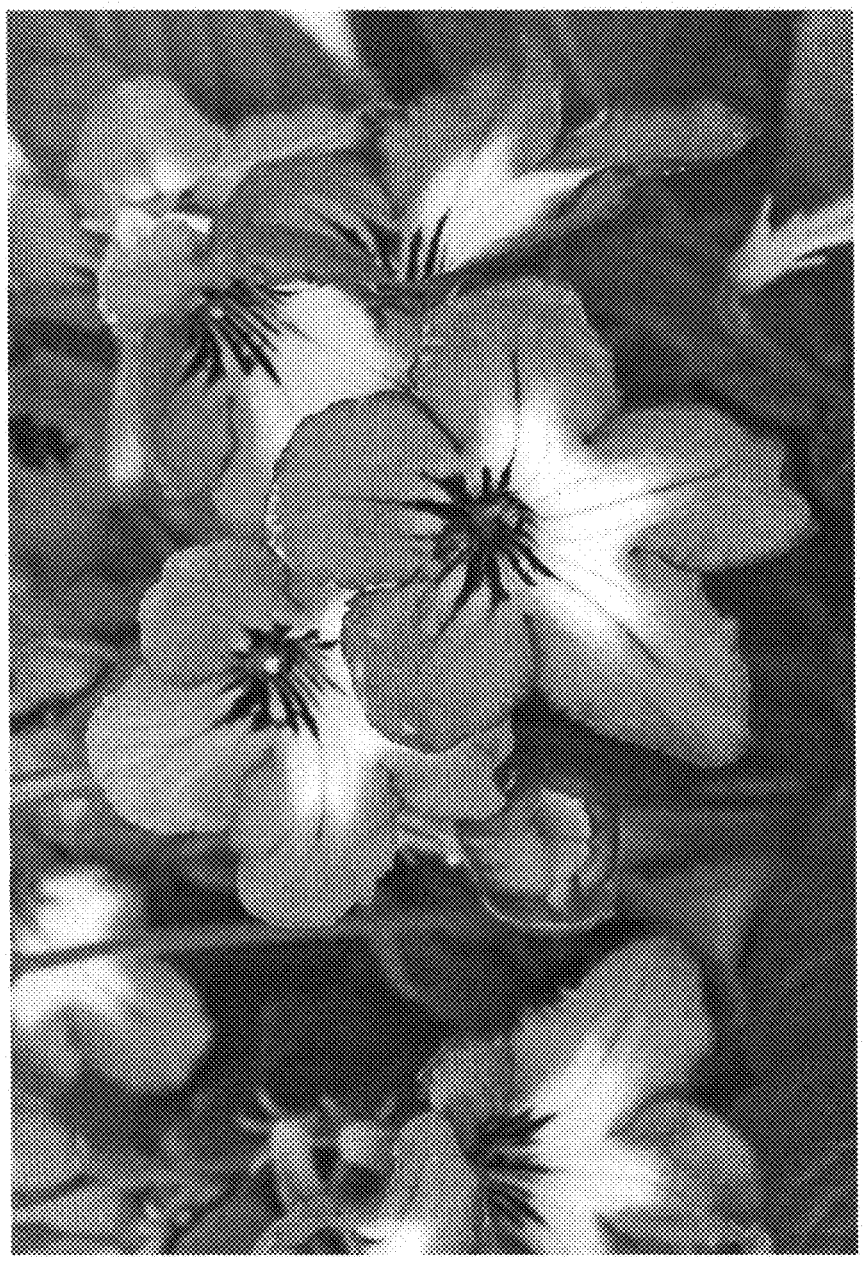

Latin name of the genus and species: *Streptocarpus* hybrid.
Variety denomination: 'SLSBW10-0'.

The new *Streptocarpus* cultivar is the product of a planned breeding program by the inventor Lynne Dibley, a citizen of United Kingdom. The breeding program was carried out at a commercial nursery in Ruthin, United Kingdom. The objective of the breeding program was to develop new *Streptocarpus* varieties for ornamental purposes.

The new variety resulted from the crossing of the seed parent, an unnamed, unpatented proprietary *Streptocarpus* seedling with the pollen parent, an unnamed, unpatented proprietary *Streptocarpus* seedling in 2008. The new variety was discovered in 2009 by the inventor in a group of seedlings resulting from the 2008 crossing, at a commercial nursery in Ruthin, United Kingdom.

Asexual reproduction of the new cultivar 'SLSBW10-0' by vegetative cuttings was first performed at Dibley's nursery in Ruthin, United Kingdom in 2009. Subsequently at least five generations have been produced from vegetative cuttings, and have shown that the unique features of this cultivar are stable and reproduced true to type.

SUMMARY OF THE INVENTION

The cultivar 'SLSBW10-0' has not observed under all possible environmental conditions. The phenotype may vary somewhat with variations in environment such as temperature, day length and light intensity, without however, any variance in genotype.

The following traits have been repeatedly observed and are determined to be the unique characteristics of 'SLSBW10-0'. These characteristics in combination distinguish 'SLSBW10-0' as a new and distinct *Streptocarpus* cultivar:

1. Small flowers size.
2. Pale violet-blue flowers
3. Multi-flowering, 6-8 per inflorescence.

COMPARISON TO THE PARENT VARIETIES

Plants of the new cultivar 'SLSBW10-0' are similar in most horticultural characteristics to plants of the unnamed, unpatented proprietary seed parent. However, the new variety has a larger overall flower and larger leaf size than the seed parent. Additionally, plants of 'SLSBW10-0' produce different colored flowers than the seed parent.

Plants of the new cultivar 'SLSBW10-0' are similar in most horticultural characteristics to plants of the unnamed, unpatented proprietary pollen parent. However, the new variety has a smaller overall flower and leaf size than the pollen parent. Additionally, plants of 'SLSBW10-0' produce flowers of the same color but with different markings than the pollen parent.

COMPARISON TO COMMERCIAL VARIETY

The new cultivar can be compared to the commercial variety 'Harlequin Blue', unpatented. Plants of the two cultivars are similar in most horticultural characteristics, however, plants of 'SLSBW10-0' produce more leaves and smaller leaves than 'Harlequin Blue'. Additionally, plants of 'SLSBW10-0' produce a longer peduncle and flower later than 'Harlequin Blue'.

The new cultivar can be compared to the commercial variety 'Bethan', unpatented. Plants of the two cultivars are similar in most horticultural characteristics, however, plants of 'SLSBW10-0' produce larger flowers with a yellow throat color not found on flower of 'Bethan'. Additionally, plants of 'SLSBW10-0' produce shorter peduncles, and no veining on flower lobe.

BRIEF DESCRIPTION OF THE PHOTOGRAPHS

The accompanying photograph in FIG. 1 illustrates in full color a typical flower of 'SLSBW10-0'.

Figure 2:
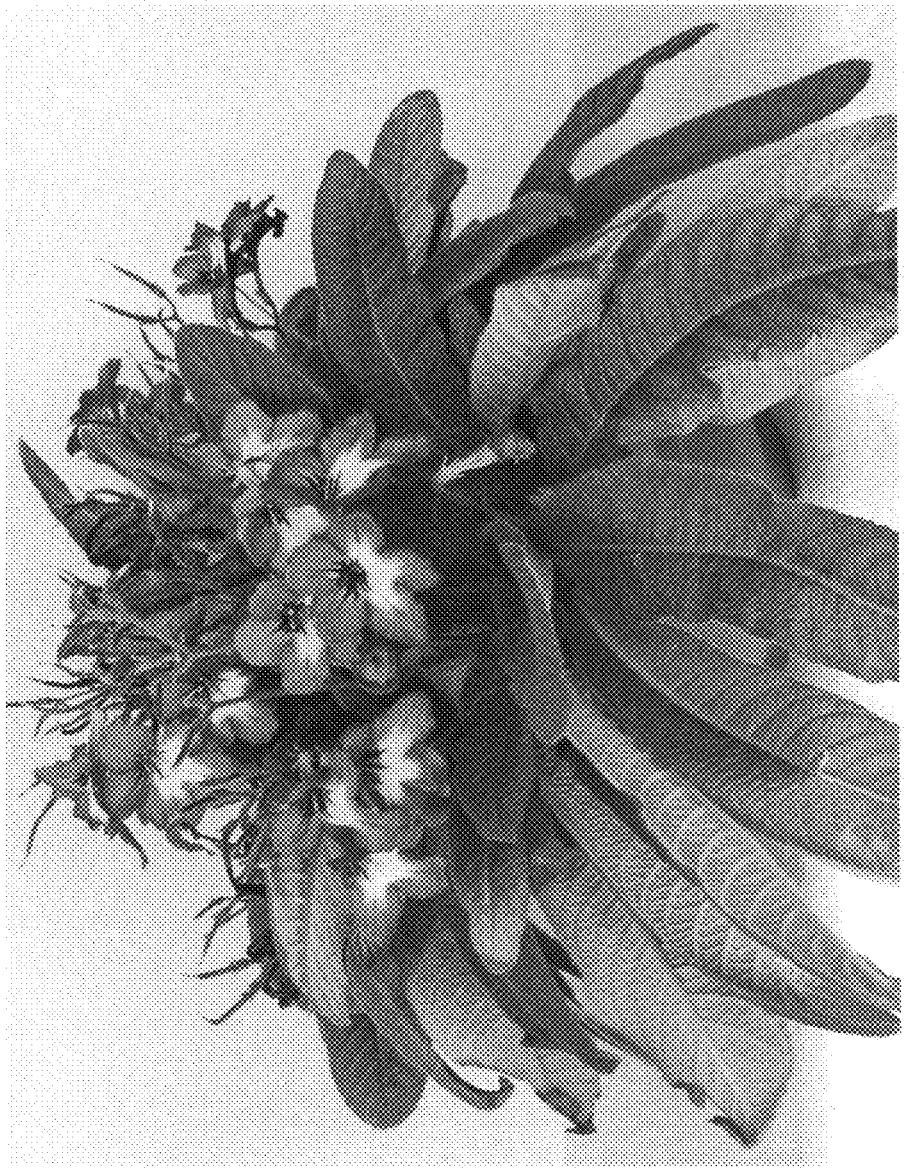

FIG. 2 illustrates a typical plant of 'SLSBW10-0' grown in a greenhouse, in an 8 inch commercial pot. Age of the plant photographed is approximately 30 weeks from a rooted cutting. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2001 except where general terms of ordinary dictionary significance are used. The following observations and measurement describe 'SLSBW10-0' plants grown in a commercial greenhouse in Oxnard, Calif. The growing temperature ranged from approximately 12° C. to 30° C. The greenhouse is subject to partial shade. General light conditions are bright, normal sunlight with some shade during the brightest part of the day. Measurements and numerical values represent averages of typical plant types.

Botanical classification: *Streptocarpus* hybrid 'SLSBW10-0'.

PROPAGATION

Time to initiate roots: About 20 to 25 days at approximately 21 to 25° C.

Root description: Fine, fibrous.

PLANT

Growth habit: Upright.

Age of the plant described: Approximately 30 weeks from a well rooted cutting.

Pot size of plant described: 12 inch pot.

Height: Approximately 22 cm from soil line to top of foliar plane. Approximately 24 cm to top of highest flower.

Plant spread: Approximately 55 cm at widest point.

Growth rate: Moderate.

Branching Characteristics: Basal rosettes of foliate, no stem, no branches.

FOLIAGE

Leaf:

*Arrangement*.—Rosette.

*Quantity*.—Average 50 to 60 leaves.

*Average length*.—Approximately 21 cm.

*Average width*.—Approximately 5.8 cm.

*Shape of blade*.—Lanceolate.

*Apex*.—Obtuse.

*Base*.—Attenuate.

*Margin*.—Crenate.

*Appearance of top surface*.—Matte.

*Appearance of bottom surface*.—Matte.

*Pubescence*.—Very short, less than 1 mm hairs, densely covering top and bottom leaf surfaces.

*Aspect*.—Somewhat undulating, overall leaf reflexes downward in older foliage.

*Color*.—Young foliage upper side: Near RHS Green 137A. Young foliage under side: Near RHS Green 138C. Mature foliage upper side: Near RHS Green 137C. Mature foliage under side: Near RHS Green 138B.

*Venation*.—Type: Pinnate. Venation color upper side: Near RHS Yellow-Green 144C. Venation color under side: Near RHS Yellow-Green 144D.

*Petiole*.—Not present, leaves sessile.

FLOWER

Natural flowering season: Continuous.

Inflorescence and flower type and habit: Racemes of 6 to 8 asymmetrical funnel shaped flowers.

Inflorescence longevity on plant: At least 2 weeks before any significant change is observed.

Approximate quantity of flowers per plant: Approximately 45 mature and immature flowers per plant.

Flowers persistent:

Inflorescence:

*Diameter of entire inflorescence*.—Approximately 10.0 cm.

*Depth of inflorescence*.—Approximately 8.0 cm.

Individual flower bud:

*Shape*.—Tubular, with spherical apex.

*Length*.—Approximately 2.9 cm.

*Diameter*.—Approximately 1.0 cm.

*Color*.—Near RHS Violet-Blue 91D with stripes Violet 86C stripes, apex Violet 86C.

Flowers:

*Flower length*.—7.0 cm.

*Flower width*.—6.0 cm.

*Upper petals* (*upper lip*).—Number: 2, fused together at base. Length: 2.5 cm. Width: 2.4 cm. Shape: Obicular. Apex: Obtuse. Margin: Shallow crenate. Texture: Velvety, all surfaces. Pubescent outer surface. Color: When opening: Inner surface: RHS Violet N88C, base striped Violet-Blue N92A. Outer surface: RHS Violet N87A. Fully opened: Inner surface: RHS Violet N88C, base striped Violet-Blue N92A. Outer surface: RHS Violet N88C. Aging: Inner surface: RHS Violet N88B, base striped Violet-Blue N92A. Outer surface: RHS Violet N87B.

*Lower petals* (*lower lip*).—Quantity: 3. Length: 2.3 cm. Width: 2.2 cm. Shape: Orbicular, fused at base. Apex shape: Obtuse. Margin: Shallow crenate, undulating. Texture: Velvety, all surfaces. Pubescent outer surface. Color: When opening: Inner surface: RHS Violet N88C, veins faintly N88A. Base blotch Yellow 4B with stripes Violet-Blue N92A. Outer surface: RHS Violet 86C, faint stripes Violet 86A. Fully opened: Inner surface: RHS Violet-blue 90D, veins faintly N88A. Base blotch Yellow 4D, and 4B with stripes Violet-Blue N92A. Outer surface: RHS Violet 86B, faint stripes Violet 86A. Aging: Inner surface: RHS Violet-blue 90D, veins faintly N88A. Base blotch White 155B with stripes Violet-Blue N92A. Outer surface: RHS Violet N87A.

*Throat*.—Length: 3.0 cm. Width: 1 cm, at widest point. Texture: glabrous, shiny inner surface. Outer surface pubescent. Color: When opening: Inner surface: RHS Violet 85C with stripes Violet-Blue N92A. Outer surface: RHS Violet 84A, faint stripes Violet 86B. Fully opened: Inner surface: RHS Violet 85C with stripes Violet-Blue N92A. Outer surface: RHS Violet 85C, stripes Violet 86A. Aging: Inner surface: RHS Violet 85D with stripes Violet-Blue N92A. Outer surface: RHS Violet-Blue 91D with stripes Violet 86B.

Sepals:

*Quantity*.—Average 5.

*Shape*.—Narrow deltate, base fused.

*Length*.—Approximately 0.7 cm.

*Width*.—Approximately 0.25 cm.

*Apex*.—Acute.

*Base*.—Fused.

*Margin*.—Entire.

*Texture*.—Highly pubescent, all surfaces.

*Color*.—Upper Surface: Near RHS Green 137A. Lower Surface: Near RHS Green 137A.

Peduncle:

*Length*.—Longest average 17 cm. Shortest average 9 cm.

*Diameter*.—Approximately 0.4 cm.

*Texture*.—Densely pubescent.

*Color*.—Near RHS Grey-Brown N199A.

*Orientation*.—Approximately 90 to 75 degree angle from rosette undulating.

Pedicel:

*Length*.—Average range 0.9 cm to 1.2 cm.

*Diameter*.—Approximately 0.3 cm.

*Texture*.—Soft, dense pubescence.

*Color*.—Near RHS Yellow-Green 146A.

*Orientation*.—Approximately 30 degree angle from peduncle. Straight, or slightly outwardly curved.

Fragrance: None.

REPRODUCTIVE ORGANS

Stamens:

*Number*.—2.

*Filament length*.—Approximately 0.8 cm, unfused section.

Anthers:

*Length*.—Approximately 0.2 cm.

*Shape*.—Bi-lobed.

*Color*.—Near RHS Greyed-Yellow 161D.

*Pollen*.—Not observed.

Pistil:

*Number*.—1.

*Length*.—Approximately 1.8 cm.

*Style*.—Length: Approximately 1.6 cm. Color: Near RHS Greyed-Purple N187A.

*Stigma*.—Shape: Bifurcate. Color: Near RHS White N155C.

OTHER CHARACTERISTICS

Seeds and fruits: Not observed.

Disease/pest resistance: Neither resistant nor susceptible to normal diseases and pests of *Streptocarpus*.

Temperature tolerance: USDA zones 9 to 11.

What is claimed is:

1. A new and distinct cultivar of *Streptocarpus* plant named 'SLSBW10-0' as herein illustrated and described.

* * * * *